United States Patent [19]

Wright

[11] Patent Number: 5,135,484

[45] Date of Patent: Aug. 4, 1992

[54] METHOD OF REMOVING PLAQUE FROM VESSELS

[75] Inventor: John T. M. Wright, Conifer, Colo.

[73] Assignee: Pioneering Technologies, Inc., Wheat Ridge, Colo.

[21] Appl. No.: 520,738

[22] Filed: May 9, 1990

[51] Int. Cl.[5] .................................... A61B 17/00
[52] U.S. Cl. ..................................... 604/28; 604/22; 604/53; 604/101; 606/159
[58] Field of Search ............... 606/159, 190, 127, 128; 128/66; 604/101, 96, 22, 43, 28, 53

[56] References Cited

U.S. PATENT DOCUMENTS

| 3,401,690 | 9/1968 | Martin | 604/22 |
|---|---|---|---|
| 3,565,062 | 2/1971 | Kuris | 606/159 X |
| 4,423,725 | 1/1984 | Baran et al. | 604/101 X |
| 4,445,509 | 5/1984 | Auth | 606/159 |
| 4,573,966 | 3/1986 | Weikl et al. | 604/101 X |
| 4,655,746 | 4/1987 | Daniels et al. | 604/101 X |
| 4,690,672 | 9/1987 | Veltrup | 604/43 |
| 4,696,668 | 9/1987 | Wilcox | 604/101 X |
| 4,729,763 | 3/1988 | Henrie | 606/159 X |
| 4,790,813 | 12/1988 | Kensey | 606/159 X |
| 4,795,438 | 1/1989 | Kensey et al. | 604/22 |
| 4,898,574 | 2/1990 | Uchiyama et al. | 606/127 X |
| 4,902,276 | 2/1990 | Zakko | 604/43 X |
| 4,950,238 | 8/1990 | Sullivan | 604/22 |

FOREIGN PATENT DOCUMENTS

| 229620 | 7/1987 | European Pat. Off. | 606/159 |
|---|---|---|---|
| 232678 | 8/1987 | European Pat. Off. | 606/159 |
| 2230283 | 1/1974 | Fed. Rep. of Germany | 606/127 |
| 3019115 | 12/1981 | Fed. Rep. of Germany | 606/159 |
| 3421390 | 12/1985 | Fed. Rep. of Germany | 606/159 |
| 3438131 | 4/1986 | Fed. Rep. of Germany | 606/127 |
| 8303356 | 10/1983 | World Int. Prop. O. | 604/101 |

*Primary Examiner*—Michael H. Thaler
*Attorney, Agent, or Firm*—Grant L. Hubbard

[57] ABSTRACT

A method of removing plaque from vessels by at least partially isolating a portion of a vessel which is partially occluded by plaque from the remainder of the vessel, forcing a slurry to flow in contact with the plaque in the vessel to abrade the plaque, and withdrawing the slurry from the vessel, and apparatus for carrying out the method, are disclosed.

3 Claims, 1 Drawing Sheet

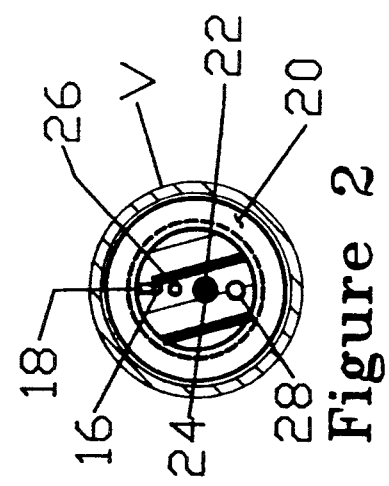
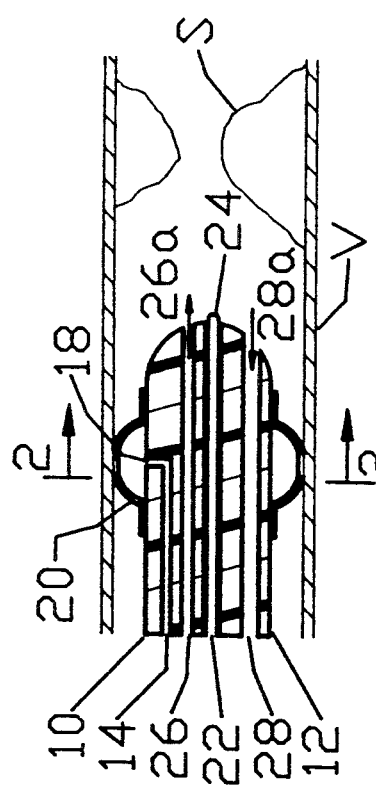
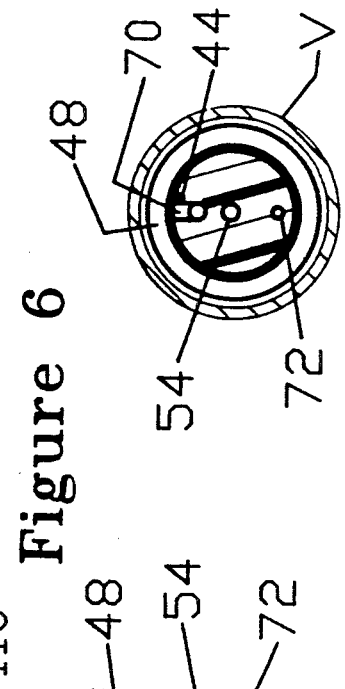
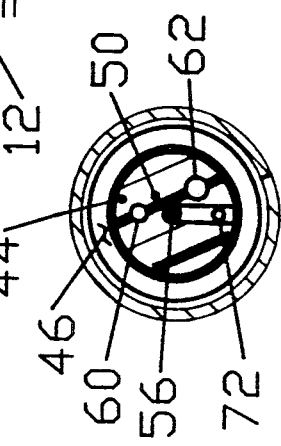
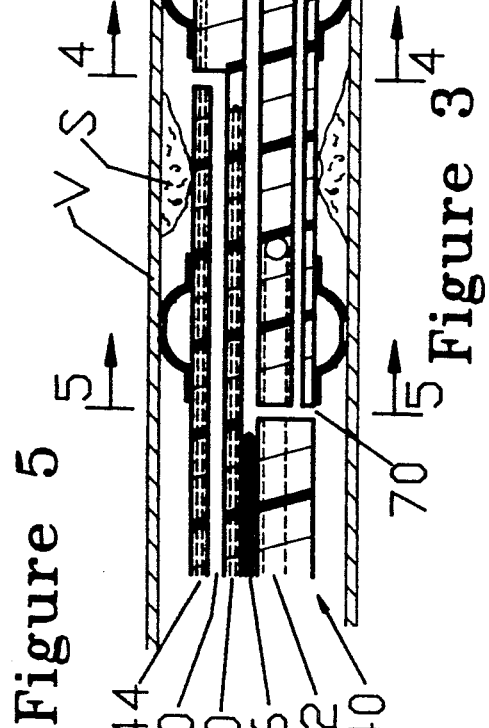

METHOD OF REMOVING PLAQUE FROM VESSELS

FIELD OF THE INVENTION

This invention relates to a catheter design and a system and a method for removing plaque from blood vessels.

BACKGROUND OF THE INVENTION

Current technology for non-surgical treatment of coronary artery disease largely involves ballon angioplasty. A catheter is threaded through a guiding catheter placed into the entrance of the coronary ostia. The balloon catheter, containing an inner guide, wire is passed through the guiding catheter. The guide wire is advanced under fluoroscopic control just past the lesion. The balloon catheter is then advanced so that the balloon is in the stenotic area and the balloon inflated to a high pressure with a contrast liquid. The plaque is hence compressed and the vessel wall dilated. Although quite successful, there is a re-stenosis rate of about 30% within six months. Laser angiography is under intensive development but has a long way to go before becoming clinically significant treatment method, if it ever does. Mechanical and electrocautery methods are also under development.

SUMMARY OF THE INVENTION

According to this invention, the removal of intra-arterial plaque is accomplished using a multi-lumen catheter to deliver an abrasive slurry to the area of stenosis. The abrasive slurry contains inert abrasive particles suspended in a radiopaque aqueous or non-aqueous liquid. The use of a radiopaque medium would allow the cardiologist to visualize the progression of plaque removal.

The invention is embodied in a system for removing plaque from vessels in a patient, which may be human or animal. The system comprises a catheter which defines an inflow lumen having an input aperture opening externally of the catheter at a first location on the catheter and a withdrawal lumen having a removal aperture opening externally of the catheter at a second location spaced from said first location, slurry input means for forcing a slurry of particles in a liquid into the input lumen and the input aperture, and slurry withdrawal means for removing slurry through the removal aperture and withdrawal lumen. The system may further comprise means for measuring fluid pressure in the vessel and controlling the pumping rate and/or withdrawal rate as a function of the measured pressure.

The catheter may include at least one inflatable balloon which forms at least one inflation lumen and, in one embodiment, includes a distal inflatable balloon and a proximal inflatable balloon and defines inflation lumen for inflating said balloons, the distal balloon being distal of the input aperture, the proximal balloon being proximal of the removal aperture.

The invention is embodied in the catheter as described and in a method of removing plaque from vessels. In this method, at least a portion of a vessel which is partially occluded by plaque is fully or partially isolated from the remainder of the vessel. A slurry is then forced to flow in contact with the plaque in the vessel to abrade the plaque. All or part of the slurry is withdrawn from the vessel. The slurry may be formed of a radiopaque liquid and abrasive particles or of liquid and particles which are insoluble in such liquid but soluble in blood serum. Water, ethyl alcohol or other liquids which are physiologically acceptable may be used in connection with conventional abrasives such as aluminum oxide or silicon carbide or with particles of a solid which are insoluble or only slightly soluble in the liquid. The particles may, of course, be insoluble in the liquid by reason of the saturation of the liquid with the material of which the particles are formed.

BRIEF DESCRIPTION OF THE DRAWING

FIG. 1 is a partial longitudinal cross-sectional view of a blood vessel with one embodiment of the catheter of this invention adjacent an area of stenosis in position to remove plaque from the vessel.

FIG. 2 is a lateral cross-sectional view of the catheter of FIG. 1 taken along lines 2—2 of FIG. 1.

FIG. 3 is a partial longitudinal, partial cross-sectional view of a blood vessel with another embodiment of the catheter of this invention encompassing an area of stenosis in position to remove plaque from the vessel.

FIG. 4 is a lateral cross-sectional view of the catheter of FIG. 3 taken along lines 4—4 of FIG. 3.

FIG. 5 is lateral cross-sectional view of the catheter of FIG. 3 taken along lines 5—5 of FIG. 3.

FIG. 6 is a schematic drawing of a pumping system which may be used as a part of the overall system of the invention.

DESCRIPTION OF THE PREFERRED EMBODIMENTS

The catheters shown in the figures and described below are intended only to describe the function of the catheters and the basic functional structure needed to carry out the desired function. The specific arrangement of conduits, etc., is presented to illustrate the functional features and not to illustrate the preferred, or even a practical construction. The precise configuration will depend upon the desired method of manufacture, the type of equipment available to the particular manufacturer, etc. For example, the catheters are shown as generally round, but they may be oval or any other shape. The exemplar catheters are shown in a configuration which could be extruded as an integral unit, but the same functional characteristics can be obtained by bundling a number of conduits.

A general overview description of both embodiments of the invention will be provided for a quick understanding, following which a detailed description of the functional structure of the catheters will be provided.

FIG. 1 shows one method of delivery of an abrasive slurry to the site of the occlusion or partial occlusion. It consists of a catheter 10 with three lumen. Lumen 14 is used to inflate balloon 20 forming a leak-proof seal with the lumen of the vessel V. The tip of the catheter is passed just proximal to the area of occlusion or stenosis S made up of plaque deposit. The balloon is inflated, and an abrasive slurry is pumped through lumen 26 and ejected against the plaque deposit as shown by the arrows 26a and withdrawn through lumen 28, as shown by arrow 28a. This arrangement will allow the opening up of completely occluded vessels.

It may be necessary to minimize the amount of residue slurry remaining or lost in the patient during treatment. In this case an alternative arrangement, shown in FIG. 3, is provided. In this embodiment, catheter 40 with two balloons 46 and 48 is used, the balloon 48 being passed through the area of stenosis S. The balloons will then be inflated via lumen 44, isolating the stenotic area between them. The abrasive slurry will be delivered through lumen 60 in the catheter 40 to scour out the area of plaque buildup. The slurry/plaque mixture will be withdrawn through lumen 62. The portion of the vessel with the highest plaque deposit, and hence the narrowest flow section, will be subjected to the maximum liquid flow velocity resulting in the highest scouring or cutting action and plaque removal rate taking place at this site.

In either case, the catheter may initially be placed by means of a guide wire, 24 in FIGS. 1 and 2 and guide wire 56 in FIGS. 3, 4 and 5. The removed plaque will be carried away by the returning slurry. Following the completion of the plaque removal process, a washing period will follow to remove most of the abrasive particles. Undoubtedly some will remain, although the amount can be minimized by careful balloon design. Deflation of the proximal balloon, followed by a withdrawal of blood or perfusate will remove particles trapped by that upstream balloon. Means may be provided to measure the pressure in the stenotic area being treated and/or to permit blood flow to bypass the stenotic area under treatment.

Use of abrasive particles in the size range of less than five microns will allow to particles to pass through, and not block, the capillaries. An accurate knowledge of the quantity of abrasive medium at the commencement of the procedure, and a careful assay of the amount of the abrasive medium collected following the procedure will allow an assessment to be made of the residue remaining in the patient. Assuming a final diameter of the vessel of 2.0 mm, a catheter diameter of 0.75 mm, and a distance between balloons, as shown in FIG. 3, of 1 cm, then the volume contained between balloons and cannula and the final lumen of the vessel will be 0.024 ml. Assuming that 90% of this volume can be swept free of the slurry, and that the slurry originally contains 30% abrasive particles by volume, then the amount of abrasive residue remaining in the patient will be 0.0006 ml or 2.4 mg., using as exemplary slurry particles aluminum oxide, which has a density 3.97 and which is available 99.999% pure. Returning now to the Figures, a detailed description of the structure for carrying out the desired function is provided.

The vessel V may be any vessel in the body but, most often, will be an arterial vessel which is largely or partially occluded by plaque as indicated by the area of stenosis S.

The catheter 10 of FIGS. 1 and 2 comprises an integrally extruded or formed elongate flexible structure 12 in which is formed the several lumen. Lumen 14 in communication through an aperture 18 communicates outside the main structure of the catheter for inflating a balloon 20 secured to the catheter in fluid-tight relation. Balloon catheters of many constructions and types are known and any number of precise structures and methods of construction may be used in making the catheters and the balloons. Many polymers, for example, are known to be quite suitable for the manufacture of catheters and balloons.

The catheter forms a generally central lumen 22 which is adapted to receive radiopaque guide wire 24. In practice, the guide wire is often inserted into the artery or other vessel and followed by X-ray visualization techniques to the location of the stenosis. At that point in the procedure, the catheter is guided over and along the wire to the desired location adjacent to the stenosis.

The catheter forms slurry lumen 26 and slurry outflow lumen 28. The abrasive slurry is pumped, by any convenient pumping mechanism, through the lumen 26 where it is ejected at high velocity toward the occlusion, as shown by the arrows 26a. The slurry, the plaque particles which are dislodged, and any other liquid or solid particles in the vicinity are withdrawn through lumen 28 by any suitable pumping means, as shown by the arrow 28a.

The catheter of FIGS. 3, 4 and 5 is similar in most respects to that shown in FIGS. 1 and 2, and is manufactured using the same body of known technology, but has additional functional structure. The catheter 40 defines a lumen 44 which communicates with and inflates proximal balloon 46 and distal balloon 48. The catheter also defines a general central lumen 54 for receiving and following guide wire 56, in the manner described with respect to guide wire 24 in the embodiment of FIG. 1. In use, the distal balloon 48 is passed through the occlusion and the balloons are inflated thereby isolating the occluded portion of the vessel between the inflated balloons. A lumen 50 may be formed to communicate to the exterior of the catheter for measuring the pressure in the isolated portion of the vessel between the balloons for monitoring the pressure therein to prevent over pressuring the vessel. The lumen also defines a slurry inflow lumen 60 and a slurry outflow lumen 62. The inflow lumen 60 communicates through the external surface of the catheter with the interior of the vessel in the zone isolated between the balloon permitting the slurry to be ejected at high velocity against the stenotic portion of the vessel. The outflow lumen 62 also communicates through the external surface of the catheter with the interior of the vessel in the zone isolated between the balloon permitting the slurry, which carries the dislodged plaque, to be removed from the isolated zone of the vessel under treatment.

The catheter may also define a passage 70 which communicates proximally of the proximal balloon with the vessel and, through either the central lumen 54 or another lumen 72, or both, distally of the distal balloon 48 thereby permitting blood flow to by-pass the portion of the vessel being treated. It may be important in certain instances that the portions of the body or organs supplied by the vessel be perfused by at least some blood flow to permit the cleaning operation to continue long enough to provide maximum benefit. For example, during the period of treatment it may be desirable to provide blood perfusion to the distal myocardium. Complete perfusion may be obtained by removing the guide wire and pumping oxygenated blood through the central lumen or permitting blood to flow around the treatment zone via a bypass lumen system.

The pumping means for providing a high velocity jet of slurry and the means for withdrawing the slurry and plaque particles may be of any type. A very simple but reliable pumping system is simply a container of slurry elevated to provide a liquid head sufficient to produce a high velocity jet and another container lower than the patient for establishing a negative head for withdrawing the slurry-plaque mixture.

During the flow of the abrasive slurry, it is desirable that the liquid pressure within the area between the two balloons remains in the physiological pressure range of 2½ psi, although higher pressures could be used if necessary. To avoid cavitation in the return flow passage of the catheter, the overall pressure drop across the catheter may not exceed about 15 psi. To reduce the pressure drop across the catheter, the major part of the overall length of the catheter may be made significantly larger in diameter than that of the distal portion. For example, the distal portion might be 10 cm in length, and of 1-2 mm in diameter, while the proximal portion might be 125 cm in length and of 3-6 mm diameter. The slurry inflow passage and the return passage would be correspondingly larger in the increased diameter section of the catheter. The large diameter for the proximal section of the catheter is permissible because only the distal 10 cm of the catheter is passed into the coronary artery. The proximal portion of the catheter passes through the larger arteries of the body. The femoral artery in the groin, the catheter entry point into the patient, is the smallest vessel that would need to be transversed.

A special delivery/exhaust positive displacement pump may also be used. This will permit the quantity of slurry withdrawn from the catheter to be controlled such that this quantity is substantially the same as that delivered though the catheter. Such a pumping arrangement may be used to prevent over extension or over pressurizing the artery during scouring. The fluid pressure in the vessel may also be monitored and used to control the pumping and/or withdrawal rate. For example, a pressure sensing lumen such as lumen 50 shown in FIGS. 3 and 4 may be used to provide a pressure feedback to adjust the relative delivery and/or withdrawal flow delivered by the pump(s). Such feedback can be achieved by any number of devices. For example, a third small capacity balancing pump, the speed and direction of which is controlled by a pressure feedback signal, may be used. Certain-volume pumps such as bellows pumps, piston pumps or peristaltic pumps, etc., may be used and the pumping rates carefully controlled as a function of the pressure in the portion of the vessel under treatment and/or the volume of material being withdrawn from that portion of the vessel.

FIG. 6 depicts, schematically, one pumping system which may used with and as part of the invention. A slurry source 100 is provided from which slurry is drawn through conduit 102 by pump 104 and delivered through conduit 106 to lumen 60, in FIG. 3, or lumen 26 in FIG. 1, to provide a jet of slurry in the treatment area. The slurry, carrying removed plaque, is withdrawn through conduit 110 by pump 112 and dumped through conduit 114 to a container 116 for disposal. Pressure may be sensed from lumen 50 in FIG. 3, or by any convenient pressure sensor. In the example, the pressure is applied through a conduit 120 to a transducer and microprocessor in controller 122 which provides control signals to the pumps 104 and 112 through conductors 124 and 126, respectively, for controlling the pumping and/or withdrawal rates.

It is convenient to provide a slurry of solid abrasive particles in a radiopaque liquid. This permits the physician to monitor the progress of plaque removal and the amount of enlargement of the vessel. Iodine-containing and other radiopaque liquids and solutions are well-known and widely used in studying circulation. Any of these liquids may be used.

The particles may be physiologically inert abrasives such as aluminum oxide or silicon carbide in the size range of less than five microns may, for example, be used. Particles of this size or smaller will pass through and not block the capillaries. Other bio-compatible particles, such as particulate hydroxyapatite, may also be used.

Particles of a substance which is solid and only slightly soluble in the carrier liquid forming the slurry but which will dissolve in blood may also be used. In this example, there are no particles remaining in the circulatory system following the procedure as described. For example, glucose (hexose) crystals slurried in ethyl alcohol in which a sufficient amount of iodine is dissolved to provide radiopacity may be used. The iodine may, of course, be omitted. Glucose is only slightly soluble in ethyl alcohol but quite soluble in water and would readily dissolve in the comparatively large volumes of blood serum into which it would be mixed following the procedure. Following the procedure using only alcohol and glucose, the patient would experience, at worst, a slight rise in blood sugar and a mild case of intoxication. Inclusion of the iodine may add the warm flush usually accompanying the use of iodine-containing radiopaque solutions.

Uric acid has very low solubility, 1 gram in 15,000 grams, of cold water and is more soluble in warm water, 1 gram in 2,000 grams of warm water. Uric acid is soluble in glycerol. A slurry of uric acid particles in cold, or even in warm, water, with or without a radiopaque constituent, may be used as the abrasive medium. Once the abrasion of plaque is complete, warm water, e.g. 105-110 F. or glycerol or a warm aqueous glycerol solution may be used to flush out the uric acid particles. Uric acid crystals are also insoluble in a acidic aqueous solution of about Ph 5.5 or lower, but relatively soluble when the Ph is raised above about 7.5 or above. A slurry of uric acid particles in an acid solution may be used as the abrasive medium. Once the plaque removal is complete, a basic solution may be used to flush out the residual uric acid particles. Many biologically acceptable acids and bases are available and may be used to provide the proper Ph. In addition, blood, being a higher Ph than the acidic slurry solution will dissolve the particles quite readily. Such particles as may remain ultimately will be excreted in the urine.

It is noted that this invention is particularly well adapted to the removal of calcified plaque which is more susceptible to abrasion and less susceptible to dissolution than ordinary uncalcified plaque. Furthermore, it is usually impossible to remove all of a plaque formation using the conventional balloon catheter - mechanical removal technique while, with this invention, the entire plaque formation can be removed and the removal monitored by X-ray visualization equipment, all with very much reduced risk of dislodging emboli which might block circulation in a distant portion of the vascular system. Obviously, the present invention could combine conventional balloon angioplasty with the techniques previously described, if this were desirable in certain instances.

Many variations are, of course, permissible and contemplated within the scope of the invention. For example, separate inflating lumen for multiple balloon catheters may be provided, and other combinations of solids and liquids may be used to obtain the desired result.

INDUSTRIAL APPLICATION

This invention is suitable for use in the practice of medicine and surgery on humans and in veterinary practice.

What is claimed is:

1. A method of removing plaque from vessels comprising the steps of:
   at least partially isolating a portion of a vessel which is partially occluded by plaque from the remainder of the vessel; and
   forcing a slurry formed of a physiologically acceptable liquid and particles which are insoluble in such liquid but soluble in blood serum to flow in contact with the plaque in the vessel to abrade the plaque.

2. The method of claim 1 further comprising the step of causing blood to flow through the catheter bypassing the isolated portion of the vessel while the slurry is forced to flow in contact with the plaque.

3. A method of removing plaque from vessels comprising the steps of:
   at least partially isolating a portion of a vessel which is partially occluded by plaque from the remainder of the vessel;
   forcing a slurry formed of a physiologically acceptable liquid and particles which are insoluble in such liquid but soluble in blood serum to flow in contact with the plaque in the vessel to abrade the plaque; and
   withdrawing at least a portion of the slurry from the vessel while continuing to force said slurry to flow in contact with the plaque in the vessel.

* * * * *